United States Patent
Beech, Jr. et al.

(10) Patent No.: US 7,119,241 B2
(45) Date of Patent: Oct. 10, 2006

(54) PROCESS FOR HANDLING CATALYST FROM AN OXYGENATE TO OLEFIN REACTION

(75) Inventors: James Harding Beech, Jr., Kingwood, TX (US); Michael Peter Nicoletti, Houston, TX (US); David Ritchie Lumgair, Jr., Craddockville, VA (US)

(73) Assignee: ExxonMobile Chemical Patents Inc., Houston, TX (US)

( * ) Notice: Subject to any disclaimer, the term of this patent is extended or adjusted under 35 U.S.C. 154(b) by 579 days.

(21) Appl. No.: 10/259,686

(22) Filed: Sep. 27, 2002

(65) Prior Publication Data

US 2004/0064006 A1    Apr. 1, 2004

(51) Int. Cl.
*C07C 1/00*    (2006.01)
*C07C 7/00*    (2006.01)

(52) U.S. Cl. .................................. 585/640; 585/809
(58) Field of Classification Search ............. 585/638, 585/639, 640, 809
See application file for complete search history.

(56) References Cited

U.S. PATENT DOCUMENTS

| | | | | |
|---|---|---|---|---|
| 3,957,464 A | * | 5/1976 | Teller ........................ | 95/196 |
| 4,231,801 A | * | 11/1980 | Dunton ....................... | 106/714 |
| 4,547,616 A | | 10/1985 | Avidan et al. .............. | 585/640 |
| 4,873,390 A | | 10/1989 | Lewis et al. ................. | 585/638 |
| 5,744,680 A | * | 4/1998 | Mulvaney et al. .......... | 585/640 |
| 6,023,005 A | | 2/2000 | Lattner et al. .............. | 585/639 |
| 6,121,504 A | * | 9/2000 | Kuechler et al. ........... | 585/640 |
| 6,137,022 A | | 10/2000 | Kuechler et al. ........... | 585/638 |
| 6,403,854 B1 | * | 6/2002 | Miller et al. ................ | 585/638 |
| 6,870,072 B1 | * | 3/2005 | Lumgair et al. ............ | 585/639 |
| 2003/0088136 A1 | | 5/2003 | Lumgair et al. ............ | 585/640 |

OTHER PUBLICATIONS

Bos et al, "Conversion of Methanol to Lower Olefins, Kinetic Modeling, Reactor Simulation, and Selection," Ind. Eng. Chem. Res. 1995, 34, 3808-3816.

Soundararajan, et al, "Modeling of Methanol to Olefins (MTO) Process in a Circulating Fluidized Bed Reactor," Fuel 80 (2001) 1187-1197.

* cited by examiner

*Primary Examiner*—Glenn Caldarcia
*Assistant Examiner*—In Suk Bullock

(57) ABSTRACT

The present invention is a process for removing catalyst fines from an effluent stream in an oxygenate to olefin process. Specifically, the catalyst fines in the effluent stream are separated from the effluent stream. Then the carbonaceous deposits are removed from the catalyst fines by incineration.

58 Claims, 1 Drawing Sheet

PROCESS FOR HANDLING CATALYST FROM AN OXYGENATE TO OLEFIN REACTION

FIELD OF THE INVENTION

The present invention relates to catalyst handling in a process for converting oxygenates to an olefin product.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming or a combination thereof.

Methanol, the preferred oxygenate for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor.

The preferred oxygenate to olefin conversion process is generally referred to as a methanol-to-olefin(s) process, where the oxygenate, e.g. methanol, is converted in a reactor to primarily ethylene and/or propylene in the presence of a catalyst—typically a molecular sieve catalyst made from a molecular sieve catalyst composition. The oxygenate to olefin reaction uses a catalyst that is maintained under operating conditions with carbonaceous deposits thereon. The carbonaceous deposits are often referred to as coke. Catalyst, for the purpose herein, is classified according to the size of the catalyst. Catalyst particles are larger than catalyst fines. Catalysts particles are typically retained in the reactor by the particle size separators that disengage or separate the catalyst particles from the effluent stream, which effluent stream passes through the particle size separators into the product recovery train. Catalyst fines are carried into the effluent stream.

Typically catalyst particles above 40 microns are added to the reactor to catalyze a reaction. During the reaction, the catalyst develops carbonaceous deposits. Withdrawing a portion of the catalyst from the reactor and burning the carbonaceous deposits off of the catalyst particles controls the aggregate amount of the carbonaceous deposits on catalyst in the reactor. As the catalyst particles travel through the reactor, they break down into smaller particles due to contact with the various parts of the reactor. As they break down in size, they eventually become catalyst fines. Catalyst fines will have the same overall amount of carbonaceous deposits as catalyst particles. Particle size separators, such as cyclones, are placed in the reactors and regenerators to retain useful catalyst particles in the reactor/regenerator system. Catalyst fines (typically less than 40 microns) are generally not retained by the particle size separators and leave the regenerator through the flue. Catalyst fines in the reactor become carried into the effluent with the product.

The effluent from an oxygenate to olefins reaction comprises a considerable amount of water when compared to other olefin forming processes. This large amount of water and the presence of catalyst with carbonaceous deposits creates unique challenges for effluent clean up and recovery. Catalyst for an oxygenate to olefin reaction is typically a molecular sieve catalyst. It is formed into catalyst particles. The presence of the catalyst fines and large quantities of water make removal and disposal of both the water and catalyst fines a unique problem in the oxygenate to olefin process.

U.S. Pat. No. 6,403,854 describes a two stage quench for use with the oxygenate conversion process. The first stage quench removes catalyst fines. But there is no guidance on how to dispose of the catalyst fines after it is removed from the effluent.

Therefore, it would be desirable to have a process for the disposal and handling of catalyst fines that improves process efficiency. It would also be advantageous to have a catalyst fines handling process that removes carbonaceous deposits from the catalyst before the catalyst fines are disposed.

SUMMARY OF THE INVENTION

This invention provides a process for the disposal and handling of catalyst (including catalyst particles and catalyst fines, more specifically catalyst fines) that, in one embodiment, improves efficiency of their removal and disposal. When catalyst fines from the reactor are redirected to the regenerator or the flue gas handling system, two catalyst handling and disposal systems are combined into one. The invention also removes carbonaceous deposits from the catalyst prior to disposal.

The process of one embodiment comprises converting an oxygenate feedstock to an olefin product in a reactor using a catalyst (typically a molecular sieve catalyst) in the form of catalyst particles. The particles have carbonaceous deposits. Some of the catalyst particles break down into catalyst fines. The catalyst typically in the form of catalyst fines leaves the reactor in the effluent stream, which comprises an olefin product and water. The catalyst in the effluent is separated from the olefin product by contacting the catalyst with a liquid quench medium. The contact of the liquid quench medium removes the catalyst from the effluent stream, including the olefin product; this contact forms a catalyst containing stream. Finally, the carbonaceous deposits on the catalyst from the catalyst containing stream are incinerated to remove at least a portion of the carbonaceous deposits from the catalyst.

According to one embodiment, the reactor is a riser reactor.

In one embodiment, the effluent stream withdrawn from the reactor comprises from about 30 wt % to about 70 wt % water, preferably, from about 35 wt % to about 70 wt % water; more preferably from about 40 wt % to about 65 wt % water based upon the total weight of the effluent stream.

According to another aspect of the invention, the weight of catalyst in the effluent stream based upon the weight of the total effluent stream is less than 1 wt %; preferably less than 0.5 wt %; more preferably from about 0.00005 wt % to about 0.5 wt %; most preferably; from about 0.0001 wt % to about 0.1 wt %.

The process of one embodiment of the present invention includes a step that separates catalyst from the effluent stream by contacting the effluent stream with a quench medium. This quenching step removes from the effluent stream, no more than about 30% by volume; preferably no more than about 20% by volume; more preferably no more than about 10% by volume; most preferably no more than about 5% by volume of the water that is present in the effluent stream when the effluent leaves the reactor.

The process of another embodiment of the present invention includes a step that separates catalyst from the effluent stream by contacting the effluent stream with a quench medium. This quenching step produces a catalyst containing stream or quench bottoms stream that has from about 0.1 wt % to about 10 wt %; preferably from about 0.1 wt % to about 5 wt %; more preferably from about 0.15 wt % to about 4 wt % of catalyst based upon the total weight of the water in the catalyst containing stream or quench bottoms stream.

In another embodiment, this quenching step is done in a solids wash device, such as a quench device or a quench tower, including but not limited to a hydrocyclone such as a venturi quench.

In one embodiment, quenching the effluent stream occurs in a two phases. The first phase quench produces a catalyst containing water stream (also referred to as a pre-quench bottoms stream, or first stage quench bottoms stream). The second phase quench removes additional water from the effluent stream and is relatively free of catalyst, when compared to the first phase. Preferably, according to this embodiment, the first phase includes a quench device selected from the group comprising a hydrocyclone separator such as a venturi quench.

For reference herein, a bottoms stream refers to the stream that is removed from the bottom of a separation tower including but not limited to a quench tower, scrubber, fractionation tower, or the like. Typical separation towers have an inlet or feed. There is also an outlet at the top end of the tower to withdraw a relatively light fraction and another outlet at the bottom end of the tower to withdraw the relatively heavy fraction. The lighter fraction is withdrawn from the tower and defines the overhead stream. The heavier fraction is withdrawn from the tower and defines a bottoms stream. The method further comprises concentrating the catalyst in the water to produce a concentrated catalyst stream.

In the most preferred embodiment of the process of the invention, the catalyst being recovered is primarily in the form of catalyst fines. The catalyst fines from the catalyst containing water stream or the concentrated catalyst stream are directed to an incinerator to incinerate the carbonaceous deposits from the catalyst fines, resulting in incinerated catalyst fines. In one embodiment, the incineration occurs in a catalyst regenerator. Preferably, the catalyst regenerator has at least one particle size separator to remove incinerated catalyst fines from the regenerator through the regenerator flue gas handling system, such that the incinerated catalyst fines are carried in the flue gas handling system of the regenerator.

In one embodiment, the incineration of catalyst, including catalyst fines, occurs in the flue gas handling system of the catalyst regenerator.

One embodiment of the present invention alternatively includes an additional step of removing the catalyst, more particularly catalyst fines, from the flue gas in the flue gas handling system. Preferably according to one embodiment, the catalyst is removed from the flue gas in an electrostatic precipitator, cyclone separator, scrubber or air filtration system, such as a baghouse. In yet another aspect of the invention, the incinerated catalyst is disposed of in a landfill, clean fill, or as an ingredient in the manufacture of cement, bricks, clay, tiles or other products where the incinerated catalyst is a suitable substitute ingredient for sand. In an alternative embodiment, the incinerated catalyst is removed from the flue gas in a scrubber. Preferably the incinerated catalyst is disposed in a wastewater treatment facility.

Another embodiment of the present invention is directed to a process for separating and disposing of catalyst fines in an oxygenate to olefins reaction system. The process comprises converting oxygenates to olefins in a reactor in the presence of catalyst particles that have carbonaceous deposits. During operation, the catalyst particles breakdown into catalyst fines. Then catalyst particles are separated from the catalyst fines and the effluent stream, which comprises olefin product and water. The catalyst fines also contain carbonaceous deposits. The catalyst fines in the effluent stream are then separated from the olefin product by condensing at least a portion of the water and contacting the portion of water with the catalyst fines to produce a dilute fines stream. The catalyst fines in the dilute fines stream are then concentrated to produce a concentrated fines stream. The concentrated fines stream is sent to an incinerator where the carbonaceous deposits on the catalyst fines in the concentrated fines stream are incinerated to remove at least a portion, or all, of the carbonaceous deposits from the catalyst fines.

In one embodiment the dilute fines stream is concentrated to a filter cake. According to one embodiment the filter cake comprises from about 50 wt % to about 99 wt % catalyst, preferably from about 65 wt % to about 95 wt % catalyst; more preferably from about 80 wt % to about 95 wt % catalyst based upon the total weight of the filter cake.

In another embodiment, it is desirable to transport the catalyst fines from a quench tower to an incinerator or incineration device through a pipeline. According to one embodiment, the concentration of the catalyst in the pipeline is below 20 wt %; more preferably from about 5 wt % to about 20 wt %; and most preferably from about 5 wt % to about 10 wt % based upon the weight of the composition of the stream in the pipeline. In another embodiment, the dilute fines stream is transported through the pipeline.

In another embodiment, the step where the catalyst fines are sent to an incinerator for incineration results in a reduction of carbonaceous deposits on the catalyst fines. Preferably, the incinerated catalyst fines are substantially free of carbonaceous deposits. By "substantially free," it is meant that more than ninety percent of the carbonaceous deposits on the catalyst are removed in the incinerator. In another embodiment, all of the catalyst fines are removed from the catalyst.

In another embodiment of the present invention, there is a process for converting a feedstock comprising an oxygenate into one or more olefin(s). The process comprises the step of contacting the feedstock with a molecular sieve catalyst composition to form one or more olefin(s) and catalyst fines comprising carbonaceous deposits. Then, an effluent stream comprising the one or more olefin(s) is withdrawn from the reactor. The effluent stream is entrained with the catalyst fines. Next, the effluent stream is contacted with a liquid quench medium to produce a first stream and a second stream, the first stream comprises substantially all the one or more olefin(s), and the second stream comprises a majority of the catalyst fines. By "substantially all," it is meant that more than 75% of the catalyst fines in the effluent stream leaving the reactor. Finally the carbonaceous deposits are removed from the catalyst fines.

In another embodiment, there is a process for removing catalyst fines comprising a carbonaceous deposit wherein the catalyst fines are formed by contacting an oxygenate with a molecular sieve catalyst composition in a reactor system comprising a reactor and a regenerator, and withdrawing from the reactor an effluent stream comprising water, catalyst fines and olefin product. The process comprises the steps of (a) separating the water and the catalyst fines from the olefin product, (b) transporting at least a portion of the water and catalyst fines to a regenerator, and (c) removing the carbonaceous deposit from the catalyst fines in the regenerator.

In another embodiment, there is a process for removing impurities from water generated by or introduced into an oxygenate to olefins reactor system. The process comprises the steps of: (a) separating an effluent stream comprising olefin(s), catalyst fines and water into a first stream comprising a majority of the olefin(s) and a second stream comprising a majority of the catalyst fines and the water; and (b) separating the second stream into a third stream comprising a majority of the catalyst fines and a fourth stream comprising a majority of the water. The quality of the fourth stream is improved because it contains less catalyst fines than the bottoms stream.

DETAILED DESCRIPTION OF THE INVENTION

Introduction

Figure 1:
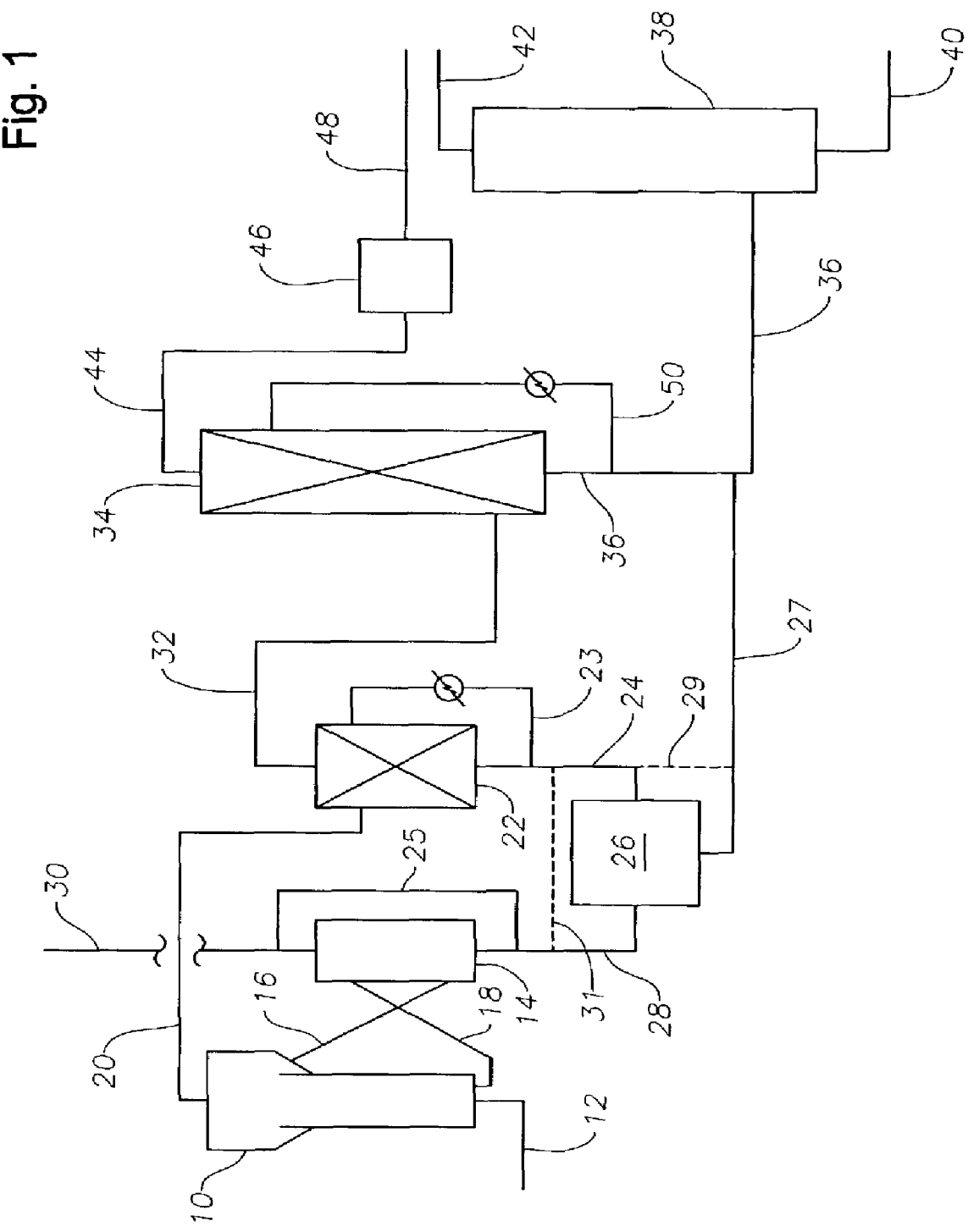
FIG. 1 illustrates one embodiment of a process for removal of catalyst from the effluent stream of a reactor and recycling catalyst back to the regenerator.

This invention provides a process that makes handling of catalyst fines more efficient, in one embodiment, by eliminating a separate catalyst fines disposal system for the catalyst fines from the reactor and catalyst fines from the regenerator. Moreover, the invention removes carbonaceous deposits from the catalyst fines before disposal of the catalyst fines. Therefore, any risk associated with the handling or disposal of carbonaceous deposits on the catalyst fines is avoided or at least mitigated.

The process comprises converting an oxygenate feedstock to an olefin product in a reactor using catalyst particles that have carbonaceous deposits in the particles. The catalyst particles break down into catalyst fines. The catalyst fines leave the reactor and become entrained in the effluent stream. In one embodiment, the effluent stream is made of at least, olefin product and water. The catalyst fines are then separated from the effluent stream. The catalyst fines are separated from the olefin product by condensing at least a portion of the water or alternatively, contacting the effluent stream with a quench medium. The quench medium or condensed water contacts the catalyst fines. The contacting removes the catalyst fines from the remainder of the effluent stream, and in particular the olefin product; this contacting forms a catalyst containing stream. Finally, the catalyst fines are incinerated to remove at least a portion of the carbonaceous deposits from the catalyst fines. The following is a description of the oxygenate to olefin process.

The Oxygenate to Olefin Process

The molecular sieve catalyst compositions are particularly useful in processes for conversion of a feedstock containing one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkylamines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols that are useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, diisopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a methanol to olefins catalyst or catalyst composition. In one embodiment, the catalyst or catalyst composition is molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

As noted, oxygenate to olefin processes use molecular sieve catalysts or catalyst compositions. The molecular sieve catalysts or catalyst compositions have molecular sieve and binder and/or matrix material. The molecular sieve catalysts are prepared according to techniques that are known to a person of ordinary skill in the art.

Molecular sieve include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof; and the large pore molecular sieves. Preferably the molecular sieve is a zeolitic or zeolitic-type molecular sieve. Alternatively, the preferred molecular sieve is an aluminophosphate (ALPO) molecular sieves and silicoaluminophosphate (SAPO) molecular sieves and substituted, preferably metal substituted, ALPO and SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including include Nalco 8676 available from Nalco Chemical Co., Naperville, Ill., and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor (s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite, zeolite-type molecular sieve catalyst, silicaluminophosphate catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 1 weight percent to about 10 weight percent based on the total weight of the feedstock including any diluent contained therein. The liquid and vapor feedstocks are preferably of similar composition, or contain varying proportions of the same or different feedstock with the same or different diluent.

The feedstock entering the reactor system is preferably converted, partially or fully, in the first reactor zone into a effluent stream that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the effluent stream containing one or more olefin(s) within the disengaging zone. Cyclones are preferred, however, gravity effects within the disengaging vessel will also separate the catalyst compositions from the effluent stream. Other methods for separating the catalyst compositions from the effluent stream include the use of plates, caps, elbows, and the like. Cyclones are particle size separators and retain catalyst above a threshold size. Catalyst below a threshold size pass through the cyclones in the effluent stream. As defined above, catalyst particles are retained by the cyclones in the reactor. Catalyst fines pass through the cyclones into the effluent stream In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from about 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock-containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See, for example, U.S. Pat. No. 5,952,538 that is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system.

The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kpaa), more preferably from about 25 psia (172 kPaa) to about 150 psia (1034 kPaa), and most preferably from about 30 psia (207 kpaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the effluent stream (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels, or the level of carbonaceous deposits, on the molecular sieve catalyst composition are measured by withdrawing from the conversion process the molecular sieve catalyst composition at a point in the process and determining its carbon content.

In one preferred embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

Product Quench and Fines Recovery

The effluent stream is withdrawn from the reactor and is passed through a solids wash, and in one embodiment a quench, to cool the effluent stream, remove a majority of the water in the effluent stream and remove solids such as catalyst fines. Alternatively, one or more heat exchangers are used to remove the heat of the effluent stream before quenching the effluent stream. The solids wash, by removing the catalyst fines, prevents the recovery train downstream from the quench from being fouled with catalyst fines.

In yet another embodiment, the effluent stream as it leaves the reactor comprises from about 30 wt % to about 70 wt % water, preferably, from about 35 wt % to about 70 wt % water; more preferably from about 40 wt % to about 65 wt % water expressed as a percentage of the total weight of the effluent stream. According to another aspect of the invention, there are catalyst fines entrained in the effluent stream. The weight of catalyst fines as a percent of the weight of the effluent stream plus entrained catalyst comprises less than 1 wt %; preferably less than 0.5 wt %; more preferably from about 0.00005 wt % to about 0.5 wt %; most preferably; from about 0.0001 wt % to about 0.1 wt %.

The regenerator as used herein includes not only the regenerator apparatus itself, but also the regenerator flue, which is a conduit or pipe that carries the incinerated gasses and incinerated catalyst fines from the regenerator.

A solids wash (or solids wash device) is defined, for purposes herein, as a device that is downstream from the reactor that removes solid particles such as catalyst including catalyst particles and catalyst fines from the effluent stream. The solids wash device is configured to contact solid phase particles suspended in the gas phase of an effluent stream with a sufficient quantity of liquid and mechanical energy to remove solid particles from the gas phase into the liquid.

According to one embodiment, the solids wash device is a quench tower or a hydrocyclonic separator such as a venturi quench (hereinafter individually referred to as a "quench device" or "quench". As noted, the effluent stream from an oxygenate to olefin reactor is quenched directly by contacting a suitable quench medium in a solids wash device or a quench tower.

A portion of the effluent stream is gaseous under quenching conditions. The gaseous stream comprises light olefins, dimethyl ether, methane, CO, $CO_2$, ethane, propane, and any water and unreacted oxygenate feedstock that is not condensed during the operation of the solids wash device. The compounds in the effluent stream, that are liquid under quenching conditions, are separated from the gaseous effluent stream as a fines stream (or quench bottoms stream). The quench bottoms stream comprises catalyst fines and quench medium, typically water, and a portion of the water quenched from the effluent stream. The quench bottoms stream also comprises a portion of the unreacted oxygenate feedstock) and a small portion of the oxygenate conversion byproducts, particularly heavy hydrocarbons (C5+).

Preferably, a quench medium is selected from a composition which remains substantially as a liquid under the quenching conditions, thus minimizing the amount of the quench medium present in the light gaseous product fraction which must undergo more expensive gaseous product processing steps to recover commercially acceptable grades of light olefin products. A preferred quench medium is selected from the group consisting of water and streams that are substantially water such as boiler feed water and demineralization water. More preferably, the quench medium is a stream that is substantially water and is selected from the several fractions of the bottoms stream from the solids wash device or "quench bottoms stream."

In particular, the quench bottoms stream is separated into a fraction that is used as a quench medium ("quench recycle fraction"). The quantity of this quench recycle fraction depends on the overall amount of heat that needs to be removed from the effluent stream in the operation of the solids wash device, and the temperature of the quench medium introduced into the solids wash device. The quench recycle fraction is cooled to a desired temperature and sent back to the solids wash device as a recycle, i.e. quench water.

According to one embodiment, it is desirable to condense substantially all of the water in the effluent stream. According to this embodiment, the weight ratio of quench medium to effluent stream ranges from about 3.5:1 to about 5.5:1; preferably from about 4.0:1 to about 5.0:1; more preferably from about 4.2:1 to about 4.7:1. The temperature of the quench medium entering the solids wash device is less than 90° C.; preferably from about 10° C. to about 60° C.; more preferably from about 20° C. to about 45° C.; most preferably about 35° C.

Optionally, the quench bottoms stream is pressurized and used for providing heat to other streams. In one embodiment, the quench bottoms stream (or any, or all of the several fractions into which the quench bottoms stream is divided, or streams from quench medium separations thereof) is used directly as a heat exchanger fluid to increase the heat content and/or temperature of the oxygenate feedstock at one or more of the stages with successively higher heat contents. Further, any of the several fractions or streams produced from the quench medium separations thereof can be used as a heat source of other streams within the overall oxygenate conversion reaction and product recovery process. For example, the quench bottoms stream is used in a heat exchanger to heat the reboiler at the bottoms of a deethanizer, demethanizer, depropanizer or a C3 splitter (depropyleneizer). Once a quench bottoms stream, or one or more fractions or streams produced from the quench medium separations is used a heat source in other parts of the process, it is cooled by such use. The cooled quench bottoms recovered from such uses is optionally returned back to the solids wash device and can be used as a quench medium.

One solids wash device of one embodiment is a cyclone separator or hydrocyclone. Cyclone separators of the type that are used for solids washes create a vortex motion that causes the heavier particles and liquids to be concentrated on the radial outward surface of the vortex and the lighter gases radially inward. The cyclone separator has a quench medium that is sprayed into its top end. The effluent stream enters the cyclone separator at a tangential inlet. The quench medium contacts the effluent stream, cools and condenses at least a portion of the effluent stream. The liquid also contacts the solids, including catalyst fines, in the effluent stream. The liquid contacting creates larger, less buoyant, water saturated particles that are forced radially outward by the vortex away from the less dense, gaseous portion of the effluent stream. One type of cyclone separator is a venturi quench. Venturi quenches are known in the art and are found in Perry's Chemical Engineers Handbook, 6th Edition, section 20, pages 93 et. seq. (1984). Cyclone separators are designed to remove all or substantially all of the solids, including catalyst fines, with relatively small amounts of water.

In certain applications of the present invention, including one where a cyclone separator is used, the step of separating removes from the effluent stream no more than 30% by volume; preferably no more than 20% by volume; more preferably no more than 10% by volume; most preferably no more than 5% by volume of the water that is present in the effluent stream when the effluent leaves the reactor.

In one aspect of the invention, the step of separating catalyst fines produces a quench bottoms stream. The concentration of catalyst fines in the bottoms stream is from about 0.1 wt % to about 10 wt %; preferably from about 0.1 wt % to about 5 wt %; more preferably from about 0.15 wt % to about 4 wt % based upon the total weight of the quench bottoms stream.

Alternatively, the catalyst fines from the quench bottoms stream (or dilute fines stream) is concentrated to produce a concentrated fines stream before being sent to the regenerator. Typically, the concentration of the catalyst fines is done with a clarification unit, filtration unit, or a centrifugal separator, Other methods known in the art for separating particulate from water can be used.

The solids wash device, including a quench device, cyclone separator, pre-quench or venturi quench produces a quench bottoms stream that comprises water and catalyst fines. The quench bottoms stream comprising water catalyst fines is directed to an incinerator to be incinerated. Alternatively, the catalyst fines from the bottoms stream of the solids wash device, or dilute fines stream, are concentrated to produce a concentrated fines stream before being sent to an incinerator (e.g., a regenerator). The concentration is done with a clarification unit, filtration unit, or a centrifugal separator. Other methods known in the art for separating particulate from water also can be used. The step of incinerating results in an incinerated catalyst fines.

An incinerator is defined as a vessel in which an oxidation reaction occurs at sufficient temperatures to remove all or a portion of the entrained carbonaceous matter, such as coke, in the catalyst. According to one embodiment, the incinerator includes but is not limited to a device selected from the group comprising catalyst regenerators, waste incinerators, lime kilns and cement kilns. Incinerators according to another embodiment include the catalyst regenerator of a reactor, typically a regenerator from an oxygenate to olefin reactor. The reactor includes the flue gas handling system of the catalyst regenerator.

In one embodiment, the regenerator is cooled by injection of water into the regenerator. In another embodiment, the water injected is the dilute fines stream or alternatively a concentrated fines stream as defined above.

Due to the small particle size of the catalyst fines, the particles produce a stable, fluid slurry readily transported, injected and distributed into the regenerator. According to one embodiment, the catalyst fines are less than 40 microns; preferably less than 20 microns; more preferably less than 10 microns.

In another embodiment, the cooling effect of the evaporation of the water in the slurry is offset by the heat of combustion of the carbonaceous deposits in the catalyst fines. In another embodiment, dilute streams are added to the regenerator. Certain streams containing catalyst require more heat to evaporate the water in the dilute stream than is produced by the burning of catalyst fines. Use of such streams can reduce the load on the catalyst cooler (i.e., the device that cools the catalyst in the regenerator or leaving the regenerator.

Since the weight of the catalyst fines is a small percentage of the catalyst recirculated, addition of a stream containing fines would have negligible effect on the size and design of the regeneration system. According to one embodiment, the amount of catalyst (eg. catalyst particles or catalyst fines and more particularly catalyst fines) in water injected in to the regenerator or regenerator flue gas handling system is below 20 wt %; more preferably from about 5 wt % to about 20 wt %; and most preferably from about 5 wt % to about 10 wt % of the total weight of the corresponding catalyst containing stream.

The catalyst fines are burned in the regenerator. However, it is advantageous, according to one aspect of the invention that the catalyst fines are removed with the flue gas of the regenerator and are not returned to the reactor with the catalyst. If catalyst fines travel with the catalyst to the reactor, they are likely to either stay in the reactor system or be removed through the cyclones of the reactor. Thus, the fines would be ultimately carried with the effluent stream to the quench system causing an inefficient cycle. Thus, it is desirable, according to one aspect of the invention, that the catalyst fines injected in the regenerator are separated from the catalyst in the regenerator/reactor system by particle size.

According to one embodiment, returning the fines into the regenerator above the catalyst bed of the regenerator improves the likelihood that the catalyst fines will be removed through the flue of the regenerator. Additionally, the catalyst can be incinerated in the flue gas handling system of the regenerator where the temperature of the flue gas is sufficiently hot to cause evaporation of the water carrying the fines and cause incineration of the carbonaceous deposits on the catalyst fines. To effect this burning, sufficient oxygen must be present in the flue gas handling system of the regenerator.

In this embodiment, the catalyst fines never enter the regenerator eliminating any co-mingling of catalyst fines with catalyst that is in the reactor/regenerator system. This embodiment is particularly advantageous when the catalyst fines become inactive as a result of the contact with the solids wash device or absorb minerals such as sodium chloride that can inactivate not only the catalyst fines but could contaminate the catalyst that is being circulated in the reactor/regenerator system.

In one embodiment, the catalyst fines are removed from the flue gas in a solids gas separation device such as a bag house, filtration apparatus or solids settling apparatus. It is preferably that the incinerated catalyst fines are substantially free of carbonaceous deposits prior to their disposal. The incinerated catalyst fines can be disposed in a landfill or a land farm or used as a sand or clay substitute in the manufacture of cement, ceramics or clay products. Accordingly, the incinerator can be a lime kiln, cement kiln, or other type of kiln.

Alternatively, the catalyst fines are removed from the flue gas in a scrubber. The incinerated catalyst fines, free of carbonaceous deposits, would be washed by a liquid solution, preferably aqueous solution thereby separating the incinerated catalyst fines from the remaining flue gas.

In one embodiment, catalyst particles are entrained in the effluent stream. Entrainment of catalyst particles can occur when a particle size separator malfunctions. Without recovery of these catalyst particles, valuable catalyst inventory can be lost. Recovery of catalyst particles is possible when the catalyst particles are washed from the effluent stream in a solids wash and then are transported to the regenerator. Unlike catalyst fines, the recovered catalyst particles will remain in the reactor/regenerator catalyst cycle. The catalyst can then return to functioning provided that catalyst was not damaged in the process of recovering and returning the catalyst particles the regenerator.

According to the invention, one solids wash system has a first and second phase. The first phase is a pre-quench, which partially condenses the water to remove the catalyst fines from the effluent stream in a concentrated portion. The second phase further condenses the water in the effluent stream to remove substantially all of the remaining water in the effluent stream. The bottoms stream of the first phase quench or pre-quench comprises a relatively concentrated amount of catalyst fines compared to a quench device that is operated to remove all of the water in the effluent stream in one stage. In one embodiment, a majority of the catalyst fines that leave the reactor are in the pre-quench bottoms stream. By majority, it is meant more than 50%.

In certain embodiments, the weight ratio of quench medium to effluent stream entering the solids wash device ranges from about 0.035:1 to about 0.55:1; preferably from about 0.1:1 to about 0.5:1; more preferably from about 0.30:1 to about 0.47:1. The temperature of the quench medium is less than 90° C.; preferably from about 10° C. to about 50° C.; preferably from about 20° C. to about 50° C.; more preferably from about 20° C. to about 40° C.; most preferably about 35° C.

In one aspect of a two stage quench embodiment of the invention, the first phase quench produces an overhead stream and quench bottoms stream. The quench bottoms stream has a concentration of catalyst fines ranging from about 0.1 wt % to about 10 wt %; preferably from about 0.1 wt % to about 5 wt %; more preferably from about 0.15 wt % to about 4 wt % based on total weight of the quench bottoms stream.

After the first phase quench, the amount of water in the overhead stream of the first phase quench device ranges from about 1 wt % to about 60 wt %; preferably from about 20 wt % to about 55 wt %; more preferably from about 30 wt % to about 50 wt % based upon the total weight of the overhead stream. The remaining effluent stream from the overhead stream of the first phase quench is directed to the inlet of the second phase quench device as described below.

The second phase is for dewatering the effluent stream. The second phase quench device quenches substantially all of the remaining water in the effluent stream. Since, most of the solids have been previously removed and the effluent stream is substantially free of solids, the bottoms stream of the second phase quench device has very little catalyst fines in the water of the bottoms stream.

The overhead of the second phase quench device is an olefin stream that has little more water than the saturation level of the remaining dewatered effluent stream. According to one embodiment, the amount of water in the effluent stream after the second phase is less than about 5 wt %; more preferably less than about 3 wt % of the total water in the effluent stream leaving the reactor.

According to one embodiment, the amount of catalyst fines in the effluent stream after the second phase quench is no greater than about 80 ppm; preferably no greater than 20 ppm; more preferably no greater than about 10 ppm based upon the total weight of the effluent stream after the second phase. Following, the second phase quench, the effluent is directed to a compression train, caustic wash, dryers and the recovery train as described below.

Product Recovery

Now that water and catalyst (eg. catalyst particles and catalyst fines, more particularly catalyst fines) is removed other steps are taken to recover product. There are many well known recovery systems, techniques and sequences that are useful in separating olefin(s) and purifying olefin(s) from the effluent stream. Recovery systems generally comprise one or more or a combination of a various separation, fractionation and/or distillation towers, columns, splitters, or trains, reaction systems and other associated equipment for example various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, a wash tower often referred to as a caustic wash tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent stream withdrawn from the reactor or converting those products produced as a result of the recovery system utilized.

In one embodiment, the effluent stream withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The effluent stream removed from a conversion process, particularly a MTO process, typically has a minor amount of hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the total weight of the effluent stream withdrawn from a MTO process, excluding water. In particular with a conversion process of oxygenates into olefin(s) utilizing a molecular sieve catalyst composition the resulting effluent stream typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a $C_x$ olefin, wherein x is a number from 2 to 4, in an amount greater than 80 percent, preferably greater than 90 weight percent, more preferably greater than 95 weight percent, and most preferably no less than about 99 weight percent, based on the total weight of the olefin.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent stream fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000 that is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I^2$) as measured by ASTM-D-1238-E in the range from 0.01 dg/min to 1000 dg/min, a melt index ratio ($I_{21}/I_2$) ($I_{21}$ is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multilayered constructions in the form of bottles, tanks, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLE

To provide a better understanding of the present invention including advantages thereof, the following example is offered with reference to FIG. 1. An oxygenate feed line 12 carries oxygenate into an oxygenate to olefins reactor 10 where the oxygenate feedstock is converted into an olefin product and other byproducts. The reaction occurs when the oxygenate feedstock is contacted with an oxygenate to olefins catalyst such as a molecular sieve catalyst composition. The catalyst that is placed in the reactor is in the form of catalyst particles. The catalyst particles develop carbonaceous deposits known as "coke." A portion of the catalyst particles are removed from the reactor into the regenerator 14 along line 16. The regenerator burns the carbonaceous deposits on the catalyst particles and returns the catalyst particles to the reactor along line 18. The catalyst particles physically break down because of the contact with the equipment in the reactor/regenerator as the catalyst particles move through the reactor/regenerator system. Particle size separators such as cyclones are in the reactor and prevent catalyst particles from leaving the reactor while catalyst fines pass through the cyclones of the reactor into effluent stream.

The effluent stream comprises, hydrocarbon byproducts, unreacted oxygenates, and oxygenate byproducts as well as water and olefins. Additionally, catalyst fines are carried in the effluent stream along line 20 to a solids wash device 22 (or first phase quench or pre-quench). Optionally, one or more heat exchangers can be placed to remove heat from the effluent stream before it enters a solids wash device such as a venturi quench.

The solids wash device 22 uses a cooled quench medium supplied along line 23 to directly quench the product effluent stream. Alternatively, the quench medium is from a fresh water source. In yet another embodiment, the quench medium for the solids wash device is supplied as cooled quench medium from line 50 (not illustrated). The effluent stream is removed from the solids wash along line 32. The quench medium and condensed portion of the effluent stream contacts the solid catalyst fines and removes them from the effluent stream along a quench bottoms stream 24.

At least a portion of quench bottoms stream 24 comprising catalyst fines and water, in one embodiment, is carried along line 31 and 28 directly to the regenerator. In another embodiment, at least a portion of quench bottoms stream is carried along line 29, 27 and 36 to the fractionator for disposal in the wastewater treatment plant. A third option is that the quench bottoms stream is carried to a solids concentration device 26. The solids concentration device includes without limitation a settling drum, a hydrocyclone, or a filtration device. The solids concentration device concentrates catalyst fines by separating catalyst fines from a portion of water that is clarified (or free of solids). Then a portion of the water is removed from the solids concentration device along line 27, according to one embodiment. A stream of concentrated catalyst fines is carried along line 28 into the regenerator 14. Adding the catalyst fines directly to the flue gas handling system 30 of the regenerator rather than adding it to the regenerator itself is preferable in one embodiment. For example, the stream in line 28 can, in one embodiment, includes matter that negatively impacts the properties of the catalyst particles. Contact of the stream in line 28 with the catalyst particles in the regenerator is avoided when stream 28 is diverted along line 25 into the flue gas handling system of the regenerator. According to one embodiment, matter that negatively impacts the properties of the catalyst, such as activity, attrition, selectivity, catalyst life, etc. includes without limitation, metal salts such as sodium salts including sodium chloride. Moreover, catalyst fines in the flue gas handling system do not increase the use of particle size separators found in the regenerator that separates the larger catalyst particles from the smaller catalyst fines.

The partially quenched (or dewatered) effluent stream from the first phase quench 22 of the present invention is carried along line 32 to a second phase quench device 34. According to one embodiment, the partially dewatered effluent stream contacts a quench medium in the second phase quench device which condenses most of the quench water and removes it from the bottoms of the quench along line 36. The bottoms of the quench device is substantially free of catalyst fines. A portion of the quench bottoms is cooled and redirected to the quench device as a quench medium along line 50.

The remainder of the quench bottoms 36 is combined with line 27 and is directed to a fractionator or methanol concentrator 38. The fractionator separates, by distillation, the methanol or other oxygenates from the water in the bottoms of the second phase quench device. The overhead stream 42 of the fractionator comprises methanol or other oxygenates or hydrocarbons that can be present in the bottoms of the second stage quench 34. The overhead stream is optionally recycled back to the reactor. The bottoms stream 40 of the fractionator or methanol concentrator 38 comprises water that optionally is sent to waste water treatment.

The overhead 44 of the second stage quench comprises substantially dewatered effluent stream. In one embodiment, only water saturated in the remaining effluent stream is present in the overhead of the second stage quench. The overhead stream is then compressed in a compression train represented by box 46. The compressed effluent stream is further processed in the olefin recovery section along line 48.

The foregoing description of the invention including but not limited to drawing and example are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

We claim:

1. A process for separating and disposing of catalyst fines in an oxygenate to olefins reaction system, the process comprising the steps of
   (a) converting oxygenates to olefins in a reactor in the presence of a catalyst having carbonaceous deposits maintained at an optimum level by a catalyst regeneration system;
   (b) withdrawing from the reactor an effluent stream comprising the olefins, the effluent stream being entrained with a portion of the catalyst in the form of catalyst fines having carbonaceous deposits;
   (c) separating the catalyst fines from the effluent stream by contacting the effluent stream with a liquid quench medium to produce a catalyst containing stream;
   (d) incinerating in an incinerator the carbonaceous deposits that are on the catalyst fines in the catalyst containing stream, said incinerator comprising a regenerator used in said catalyst regeneration system; and
   (e) removing said catalyst fines from said regenerator without returning said catalyst fines to said reactor.

2. The process of claim 1, wherein the reactor is a turbulent bed reactor.

3. The process of claim 1, wherein the reactor is a riser reactor.

4. The process of claim 1, wherein the catalyst is molecular sieve catalyst.

5. The process of claim 1, wherein the effluent stream further comprises from about 30 wt % to about 70 wt % water based upon the total weight of the effluent stream.

6. The process of claim 1, wherein the effluent stream further comprises from about 35 wt % to about 70 wt % water based on the total weight of the effluent stream.

7. The process of claim 1, wherein the effluent stream further comprises from about 40 wt % to about 65 wt % water based upon the total weight of the effluent stream.

8. The process of claim 1, wherein the effluent stream comprises less than 1 wt % catalyst based upon the total weight of the effluent stream.

9. The process of claim 1, wherein the effluent stream comprises less than 0.5 wt % catalyst based upon the total weight of the effluent stream.

10. The process of claim 1, wherein the effluent steam comprises from about 0.00005 wt % to about 0.5 wt % catalyst fines based upon the total weight of the effluent stream.

11. The process of claim 1, wherein the effluent stream comprises from about 0.0001 wt % to about 0.1 wt % catalyst fines based upon the total weight of the effluent stream.

12. The process of claim 1, wherein the effluent stream further comprises water and the catalyst containing stream has no more than 35% by volume of the total volume of water in the effluent stream.

13. The process of claim 12, wherein the catalyst containing stream has no more than 30% by volume of the total volume of water in the effluent stream.

14. The process of claim 12, wherein the catalyst containing stream has no more than 25% by volume of the total volume of water in the effluent stream.

15. The process of claim 12, wherein the catalyst containing stream has no more than 10% by volume of the total volume of water in the effluent stream.

16. The process of claim 12, wherein the catalyst containing stream has no more than 5% by volume of the total volume of water in the effluent stream.

17. The process of claim 1, wherein the catalyst containing stream has from about 0.1 wt % to about 10 wt % of catalyst fines based upon the total weight of the catalyst containing stream.

18. The process of claim 17, wherein catalyst containing stream has from about 0.1 wt % to about 5 wt % catalyst fines based upon the total weight of the catalyst containing stream.

19. The process of claim 17, wherein the catalyst containing stream has from about 0.15 wt % to about 4 wt % catalyst fines based upon the total weight of the catalyst containing stream.

20. The process of claim 1, wherein the catalyst containing stream comprises catalyst fines and water, the process further comprising concentrating the catalyst fines in the catalyst containing stream to produce a concentrated catalyst stream having from about 5 wt % to about 95 wt % catalyst fines based upon the total weight of the concentrated catalyst stream.

21. The process of claim 20, wherein the concentrated catalyst stream has from 10 wt % to about 90 wt % catalyst fines based upon the total weight of the concentrated catalyst stream.

22. The process of claim 20, wherein the concentrated catalyst stream has from 20 wt % to about 90 wt % catalyst fines based upon the total weight of the concentrated catalyst stream.

23. The process of claim 1, wherein the step of incinerating in said catalyst regenerator produces incinerated catalyst fines.

24. The process of claim 23, wherein the catalyst regenerator has at least one particle size separator to remove incinerated catalyst fines into the regenerator gas handling system without removing regenerated catalyst particles.

25. The process of claim 24, wherein the incinerated catalyst fines are removed from the regenerator in a flue gas handling system, the catalyst is carried by the flue gas.

26. The process of claim 25, wherein the incinerated catalyst fines are removed from the flue gas in a baghouse.

27. The process of claim 25, wherein the incinerated catalyst fines are removed from the flue gas in a scrubber.

28. The process of claim 25, wherein the incinerated catalyst fines are disposed of in a landfill, land farm, or kiln.

29. The process of claim 1, wherein the step of (c) of separating the catalyst fines is done in a solids wash device.

30. The process of claim 1, wherein the step of (c) of separating the catalyst fines is done in a quench device.

31. The process of claim 25, wherein the catalyst fines are disposed of in a waste water treatment facility.

32. A process of separating and disposing of catalyst fines in an oxygenate to olefins reaction system, the process comprising the steps of:
   (a) converting oxygenates to olefins in a reactor in the presence of catalyst particles which contain carbonaceous deposits maintained at an optimum level by a catalyst regeneration system;
   (b) separating the catalyst particles from the effluent stream comprising olefin product and water, the effluent stream being entrained with catalyst fines having carbonaceous deposits;
   (c) separating the catalyst fines from the olefin product by contacting the catalyst fines with a quench medium to produce a dilute fines stream;
   (d) concentrating the dilute fines stream to produce a concentrated fines stream;
   (e) removing in an incinerator at least a portion of the carbonaceous deposits from the catalyst fines from the concentrated fines stream, said incinerator comprising a regenerator used in said catalyst regeneration system; and
   (f) removing said catalyst fines from said regenerator without returning said catalyst fines to said reactor.

33. The process of claim 32, wherein the quench medium is condensed water from the effluent stream.

34. The process of claim 1 wherein the step (c) of separating is done in a hydrocyclone.

35. The process of claim 1, wherein the step (c) of separating is done in a venturi quench.

36. The process of claim 32, wherein the effluent stream comprises less than 1 wt % catalyst based upon the total weight of the effluent stream.

37. The process of claim 32, wherein the effluent stream comprises less than 0.5 wt % catalyst based upon the total weight of the effluent stream.

38. The process of claim 32, wherein the effluent stream comprises from about 0.00005 wt % to about 0.5 wt % catalyst based upon the total weight of the effluent stream.

39. The process of claim 32, wherein the effluent stream comprises from about 0.0001 wt % to about 0.1 wt % catalyst based upon the total weight of the effluent stream.

40. The process of claim 32, wherein the dilute fines stream contains no more than 30% by volume of water based upon the total volume of water in the effluent stream.

41. The process of claim 32, wherein the dilute fines stream contains no more than 20% by volume of the water based upon the total volume of water in the effluent stream.

42. The process of claim 32, wherein the dilute fines stream contains no more than 15% by volume of the water based upon the total volume of water in the effluent stream.

43. The process of claim 32, wherein the dilute fines stream contains no more than 10% by volume of the water based upon the total volume of water in the effluent stream.

44. The process of claim 32, wherein the dilute fines stream contains no more than 5% by volume of the water based upon the total volume of water itt the effluent stream.

45. The process of claim 32, wherein the dilute fines stream contains from about 0.1 wt % to about 10 wt % catalyst fines based upon the weight of the dilute fines stream.

46. The process of claim 32, wherein the dilute fines steam contains from about 0.1 wt % to about 5 wt % catalyst fines bused upon the weight of the dilute fines stream.

47. The process of claim 32, wherein the dilute fines stream contains at least 0.15 wt % to about 4 wt % catalyst fines based upon the weight of the dilute fines stream.

48. The process of claim 32 wherein the concentrated fines stream contains from about 20 wt % to about 50 wt % catalyst fines based upon the weight of the concentrated fines stream.

49. The process of claim 48, wherein the catalyst regenerator has at least one particle size separator to separate catalyst fines and regenerator flue gas from catalyst particles.

50. The process of claim 49, wherein the incinerated catalyst fines are removed from the flue gas.

51. The process of claim 49, wherein the incinerated catalyst fines are removed from the flue gas in a baghouse.

52. The process of claim 49, wherein the incinerated catalyst fines are disposed of in a landfill, and farm, or lime kiln.

53. The process of claim 32, wherein the step of separating the catalyst fines is done in a solids wash device.

54. The process of claim 32, wherein the ratio of heat of combustion of carbonaceous deposits on the catalyst fines to the heat of vaporization of water in the concentrated fines stream ranges from about 0.01:1 to about 35:1.

55. The process of claim 32, wherein the ratio of heat of combustion of carbonaceous deposits on the catalyst fines to the heat of vaporization of water in the concentrated fines stream ranges from about 0.01:1 to about 20:1.

56. The process of claim 32, wherein the ratio of heat of combustion of carbonaceous deposits on the catalyst fines to the heat of vaporization of water in the concentrated fines stream ranges from about 0.01:1 to about 10:1.

57. The process of claim 32, wherein the concentrated fines stream comprises from about 5 wt % to about 20 wt % of catalyst fines based upon the total weight of the concentrated fines stream.

58. The process of claim 32 wherein the concentrated fines stream comprises from about 50 wt % to about 99 wt % catalyst fines based upon the total weight of the concentrated fines stream.

* * * * *